US012776393B1

(12) United States Patent
Wehner et al.

(10) Patent No.: US 12,776,393 B1
(45) Date of Patent: Oct. 27, 2026

(54) SYSTEM AND METHOD FOR AGGREGATE DATA SNAPSHOT EXTRACTION AND OPTIMIZED BULK LOCK, EDIT, AND FREEZE

(71) Applicant: Veeva Systems Inc., Pleasanton, CA (US)

(72) Inventors: Margaret Wehner, San Francisco, CA (US); Quentin Paresys, Fremont, CA (US); Raymond T. Letulle, Jr., Orinda, CA (US); Drew Garty, Madison, WI (US)

(73) Assignee: Veeva Systems Inc., Pleasanton, CA (US)

( * ) Notice: Subject to any disclaimer, the term of this patent is extended or adjusted under 35 U.S.C. 154(b) by 0 days.

(21) Appl. No.: 18/356,805

(22) Filed: Jul. 21, 2023

(51) Int. Cl.
*G06F 16/26* (2019.01)
*G06F 16/215* (2019.01)
*G16H 10/20* (2018.01)

(52) U.S. Cl.
CPC ........... *G16H 10/20* (2018.01); *G06F 16/215* (2019.01); *G06F 16/26* (2019.01)

(58) Field of Classification Search
CPC ........ G16H 10/20; G06F 16/215; G06F 16/26
See application file for complete search history.

(56) References Cited

U.S. PATENT DOCUMENTS 7,054,823 B1 * 5/2006 Briegs .................... G16H 10/20 707/999.001
7,921,125 B1 * 4/2011 Houriet, Jr. ............ G16H 10/20 707/754
10,902,081 B1 * 1/2021 Gassner ............... G06Q 10/103
12,007,870 B1 * 6/2024 Jain ..................... G06F 11/3438
2004/0078216 A1 * 4/2004 Toto ....................... G16H 10/20 707/999.1
2005/0240443 A1 * 10/2005 Salman .................. G16H 10/20 705/3
2010/0185464 A1 * 7/2010 Houriet, Jr. ............ G16H 10/20 705/317
2014/0324553 A1 * 10/2014 Rosenberg ............ G16H 10/20 705/7.41
2015/0057177 A1 * 2/2015 Borrebaeck .......... C12Q 1/6886 435/7.1
2016/0085943 A1 * 3/2016 de Vries ................. G16H 10/20 705/2
2016/0231315 A1 * 8/2016 Harrop .................... A61P 35/00
(Continued)

*Primary Examiner* — Mohammad S Rostami

(57) ABSTRACT

Systems and methods for aggregating clinical trial data and performing optimized bulk lock, edit and freeze operations to clean the extracted data. A user interface is provided for access to a medical data management system to define one or more site criteria, one or more subject criteria, an event window based on clinical trial study schedule events or a calendar date range, one or more identified log forms for specified date references, and one or more identified criteria for ready states. Clinical trial source data fulfilling the defined criteria is extracted to form an aggregated clinical trial data snapshot. Data management operations for the extracted clinical trial source data that fulfills the defined site criteria, the defined subject criteria, the defined event window, the identified log forms for specified date references, and the identified criteria for ready states can be restricted and rescinded to clean the clinical trial data efficiently.

16 Claims, 10 Drawing Sheets

(56) References Cited

U.S. PATENT DOCUMENTS

| | | | | |
|---|---|---|---|---|
| 2019/0026849 | A1* | 1/2019 | DeMeyer | G16Z 99/00 |
| 2020/0168304 | A1* | 5/2020 | Manasco | G16H 10/20 |
| 2020/0381087 | A1* | 12/2020 | Ozeran | G06F 16/31 |
| 2021/0090694 | A1* | 3/2021 | Colley | G16B 30/00 |
| 2024/0100072 | A1* | 3/2024 | Facheris | A61P 25/28 |

* cited by examiner

FIG. 8
800
801
802
803
CDMS
Details
Filter Scope
Forms
Log Forms
Ready States

FIG. 9
900
CDMS
Operation History
901
902
903

SYSTEM AND METHOD FOR AGGREGATE DATA SNAPSHOT EXTRACTION AND OPTIMIZED BULK LOCK, EDIT, AND FREEZE

TECHNICAL FIELD

The present disclosure relates generally to platforms and approaches to aggregating and cleaning data, particularly in health-related data, including clinical trial electronic data capture (EDC), clinical lab data, and so forth.

BACKGROUND

In clinical trials, data cleaning is the process of detecting, diagnosing, and editing faulty data. Data cleaning is an essential step to reducing errors from various sources and their impact on clinical study results. Errors can occur despite careful clinical study design, conduct, and implementation of error-prevention strategies. For instance, two common aspects of data cleaning are statistical outlier detection and handling of missing data. Typically, data cleaning involves repeated cycles of screening, diagnosis, and editing of suspected data abnormalities. This allows accurate data to which analysis can be made.

The current workflow is piecemeal, as each data element can be locked (e.g., subject by subject) as it is being reviewed. This current implementation is largely considered best practice because it reduces the unnecessary locking of data and ensures that the data is likely examined as part of the locking process. However, the practical reality is that there are other use cases where this piecemeal review is tedious and time consuming. There is a need to provide a mechanism to quickly lock/unlock or freeze/unfreeze large numbers of events across casebooks within the study more efficiently.

SUMMARY

Embodiments disclosed in the present document provide a machine-implemented method and system for aggregate data snapshot extraction and optimized bulk lock, edit and freeze. The computer-implemented method for optimized processing of clinical trial data in a clinical trial management system comprising: enabling display of a user interface for managing aggregated clinical trial source data, wherein the clinical trial source data is clinical trial data obfuscated to remove patient defining information and stored as electronic data capture (EDC) data in a first repository in the clinical trial management system; defining one or more site criteria, wherein the site criteria includes a selected subset of sites that are flagged with clinical trial source data of interest for subsequent analysis and data cleansing; defining one or more subject criteria, wherein the subject criteria includes a selected subset of subjects that are flagged with clinical trial source data of interest for subsequent analysis and data cleansing; defining an event window, wherein the event window includes a selected subset of clinical trial study schedule events of interest for subsequent analysis and data cleansing; identifying log forms for specified date references that are flagged with clinical trial source data of interest for subsequent analysis and data cleansing; identifying one or more criteria for ready states, wherein the ready states include conditions that require additional user action before restricting data management operations; extracting clinical trial source data that fulfills the defined site criteria, the defined subject criteria, the defined event window, the identified log forms for specified date references, and the identified criteria for ready states to form an aggregated clinical trial data snapshot; display the aggregated clinical trial data snapshots on the user interface, wherein the clinical trial data snapshot includes a table of clinical trial source data entries broken down numerically by at least one of the defined site criteria, the defined subject criteria, the defined event window, the identified log forms for specified date references, and the identified criteria for ready states; and_restricting data management operations for the extracted clinical trial source data that fulfills the defined site criteria, the defined subject criteria, the defined event window, the identified log forms for specified date references, and the identified criteria for ready states.

BRIEF DESCRIPTION OF THE DRAWINGS

For a more complete understanding of the present application and its advantages, references are now made to the following description taken in conjunction with the accompanying drawings, in which like reference numbers indicate like features.

Although similar reference numbers may be used to refer to similar elements for convenience, it can be appreciated that each of the various example embodiments may be considered to be distinct variations.

The present embodiments will now be described hereinafter with reference to the accompanying drawings, which form a part hereof, and which illustrate example embodiments which may be practiced. As used in the disclosures and the appended claims, the terms "embodiment" and "example embodiment" do not necessarily refer to a single embodiment, although it may, and various example embodiments may be readily combined and interchanged, without departing from the scope or spirit of the present embodiments. Furthermore, the terminology as used herein is for the purpose of describing example embodiments only, and are not intended to be limitations. In this respect, as used herein, the term "in" may include "in" and "on," and the terms "a", "an", and "the" may include singular and plural references. Furthermore, as used herein, the term "by" may also mean "from," depending on the context. Furthermore, as used herein, the term "if" may also mean "when" or "upon," depending on the context. Furthermore, as used herein, the words "and/or" may refer to and encompass any and all possible combinations of one or more of the associated list items.

DETAILED DESCRIPTION

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology is not limited to the specific details set forth herein and may be practiced without these specific details. In some instances, well-known structures and components are shown in block diagram form in order to avoid obscuring the concepts of the subject technology.

Figure 1:
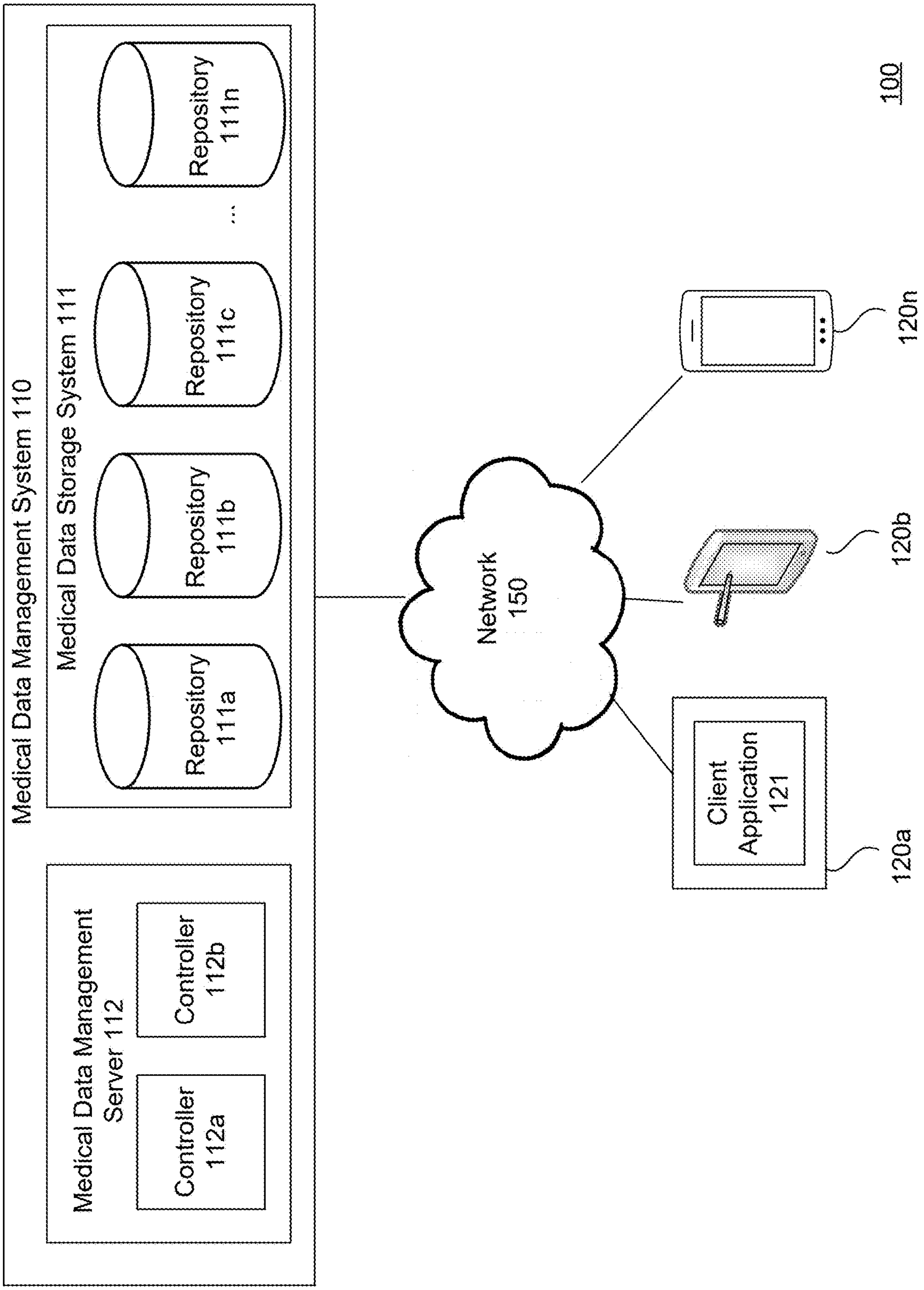
FIG. 1 illustrates an example high level block diagram of a medical data management architecture wherein the present invention may be implemented.

FIG. 1 illustrates an example high level block diagram of a medical data management architecture 100 wherein the present invention may be implemented. As shown, the architecture 100 may include a medical data management system 110, and a plurality of user computing devices 120*a*, 120*b*, . . . 120*n*, coupled to each other via a network 150. The medical data management system 110 may include a medical data storage system 111 and a medical data management server 112. The medical data storage system 111 may have two or more repositories, e.g., 111*a*, 111*b*, 111*c*, . . . and 111*n*. The network 150 may include one or more types of communication networks, e.g., a local area network ("LAN"), a wide area network ("WAN"), an intra-network, an inter-network (e.g., the Internet), a telecommunication network, and peer-to-peer networks (e.g., ad hoc peer-to-peer networks), which may be wired or wireless.

The computing devices 120*a*-120*n* may be any machine or system that is used by a user to access the medical data management system 110 via the network 150, and may be any commercially available computing devices including laptop computers, desktop computers, mobile phones, smart phones, tablet computers, netbooks, and personal digital assistants (PDAs). A client application 121 may run from a user computing device, e.g., 120*a*, and access data in the medical data management system 110 via the network 150.

The medical data storage system 111 may store medical data that client applications (e.g., 121) in user computing devices 120*a*-120*n* may access and may be any commercially available storage devices. Each content repository (e.g., 111*a*, 111*b* or 111*n*) may store a specific category of data, and allow users to interact with its data in a specific business context. It should be appreciated that content repositories may be separate logic sections in a same storage device.

The medical data management server 112 is typically a remote computer system accessible over a remote or local network, such as the network 150. The medical data management server may store a medical data management controller 112*a* and a medical data collection controller 112*b* for controlling management and collection of the medical data, including the method to be discussed with FIG. 7. The medical data management server 112 could be any commercially available computing devices. Although only one server is shown, it should be appreciated and the medical data management system 110 may have a plurality of servers and the controllers 112*a* and 112*b* may be in separate servers. A client application (e.g., 121) process may be active on one or more user computing devices 120*a*-120*n*. The corresponding server process (e.g., 112*a* and 112*b*) may be active on the medical data management server 112. The client application process and the corresponding server process may communicate with each other over the network 150, thus providing distributed functionality and allowing multiple client applications to take advantage of the information-gathering capabilities of the medical data management system 110.

In one implementation, the architecture 100 may be used for aggregating and managing medical data, e.g., clinical trial data. A first repository (e.g., 111*a*) may be used by a first sponsor (e.g., a pharmaceutical company) to store a first study design received from a first computing device (e.g., 120*a*). The first study design may define the infrastructure and lifecycle of the study, and may comprise rules (e.g., for queries, derived values, notifications and displaying events, forms and items), a casebook (i.e., a doctor's binder), event groups, events (e.g., patients visits), forms which comprise segregated sections and fields, item groups and items. In one example, a study design may define a particular study, i.e., each patient may have ten visits, and each visit may have three forms. There may be a workflow associated with each visit, e.g., what needs to be done at each visit.

In one implementation, the first study design may be stored as definition objects in the first repository 111*a*, specifying what is required to happen on each site during the study. The first repository 111*a* may also store electronic records of the first study. In one implementation, the electronic records may be EDC data. Patient clinical trial source data may be captured at the user computing devices, and the aggregated and obfuscated data may be stored as EDC data in the first repository 111*a*.

The second repository 111*b* may be used by a first site (e.g., a hospital) of the first study to store clinical trial source data from a second user computing device (e.g., 120*b*), and a third repository (e.g., 111*c*) may be used by a second site of the first study to store clinical trial source data from a third user computing device (e.g., 120*c*). The clinical trial source data (e.g., three blood pressure values of a patient taken during one visit) in the second repository 111*b* may be converted to EDC data (e.g., the average of the three blood pressure values) automatically, and then stored in the first repository 111*a* as EDC data. Similarly, the clinical trial source data in the third repository 111*c* may be converted to EDC data automatically, and then stored in the first repository 111*a* as EDC data. In one implementation, the clinical trial source data may be converted to the EDC data at the client application 121, and the EDC data is transmitted to the medical data management server 112. In one implementation, the clinical trial source data may be transmitted to the repository 111*b* or 111*c* via the medical data management server 112, and converted to the EDC data at the medical data management server 112. The EDC data is then stored in the repository 111*a*. Data in the second repository 111*b* and the third repository 111*c* may be synchronized with that in the first repository 111*a* regularly or from time to time when new data entries are received from user computing devices. The first study design may be transmitted to the second repository 111*b* and the third repository 111*c*. The second repository and the third repository may be synchronized with the first repository for updates to the first study design.

In another implementation, a first repository (e.g., 111*a*) may be used by a sponsor (e.g., a pharmaceutical company) using a first computing device (e.g., 120*a*) to store EDC data received from a site (e.g., local lab) using a second computing device (e.g., 120*b*). The EDC data input by the second computing device may contain questionable content requiring verification. Queries may be created by the first computing device and managed by the medical data management server 112. The site (e.g., a local lab) may use the first repository (e.g. 111*a*) from a second user computing device (e.g., 120*b*) to answer the queries managed by the medical data management server 112. Upon satisfactory response, the query can be closed by the medical data management server 112. Alternatively, the first computing device (e.g., 120*a*) may create a subsequent query to be managed by the medical data management server 112.

In one implementation, the medical data management system 110 may be a multi-tenant system where various elements of hardware and software may be shared by one or more customers. For instance, a server may simultaneously process requests from a plurality of customers (e.g., sponsors, and clinical sites), and the medical data storage system 111 may store content for a plurality of customers (e.g., sponsors, and clinical sites). In a multi-tenant system, a user is typically associated with a particular customer. In one example, a user could be an employee of one of a number of pharmaceutical companies or clinical trial sites which are tenants, or customers, of the medical data management system 110.

In one embodiment, the medical data management system 110 may run on a cloud computing platform. Users can access content on the cloud independently by using a virtual machine image, or purchasing access to a service maintained by a cloud database provider.

In one embodiment, the medical data management system 110 may be provided as Software as a Service ("SaaS") to allow users to access the medical data management system 110 with a thin client.

Figure 2:
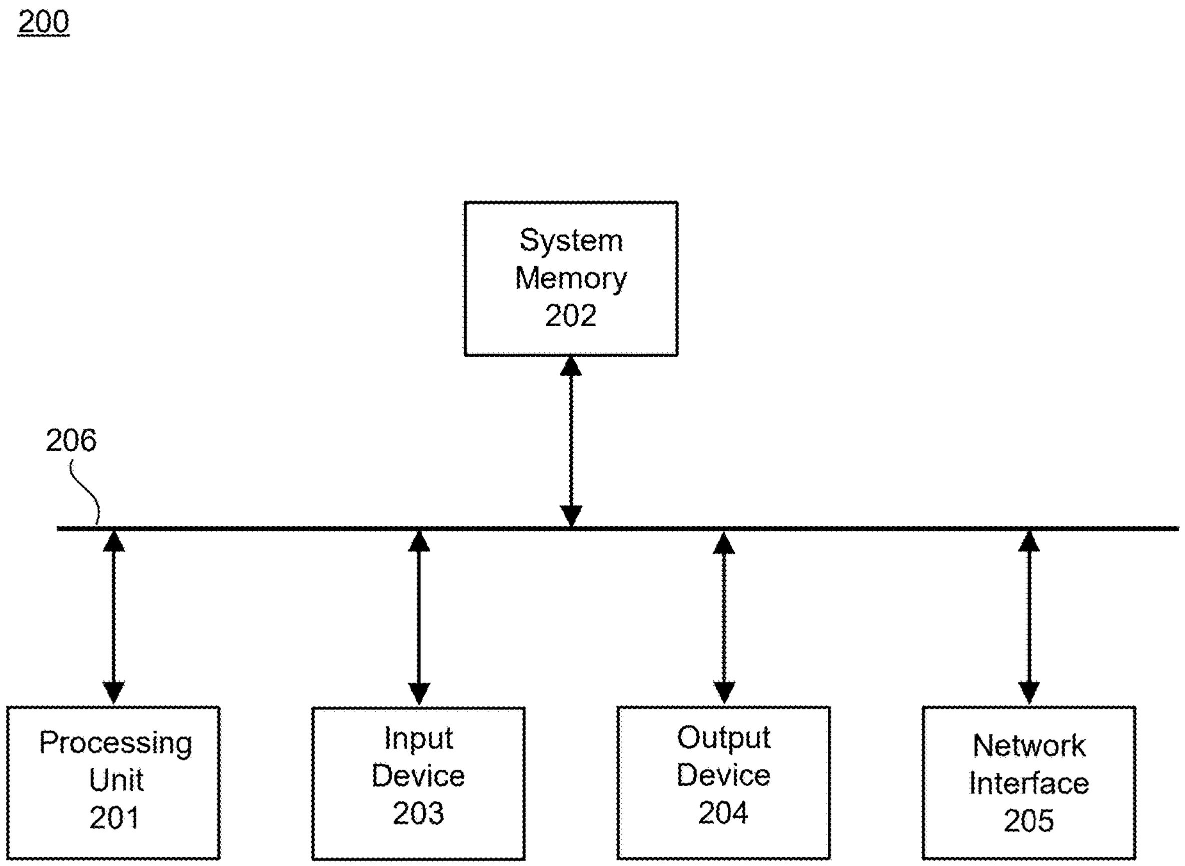
FIG. 2 illustrates an example block diagram of a computing device.

FIG. 2 illustrates an example block diagram of a computing device 200 which can be used as the user computing devices 120*a*-120*n*, and the medical data management server 112 in FIG. 1. The computing device 200 is only one example of a suitable computing environment and is not intended to suggest any limitation as to scope of use or functionality. The computing device 200 may include a processing unit 201, a system memory 202, an input device 203, an output device 204, a network interface 205 and a system bus 206 that couples these components to each other.

The processing unit 201 may be configured to execute computer instructions that are stored in a computer-readable medium, for example, the system memory 202. The processing unit 201 may be a central processing unit (CPU).

The system memory 202 typically includes a variety of computer readable media which may be any available media accessible by the processing unit 201. For instance, the system memory 202 may include computer storage media in the form of volatile and/or nonvolatile memory such as read only memory (ROM) and/or random access memory (RAM). By way of example, but not limitation, the system memory 202 may store instructions and data, e.g., an operating system, program modules, various application programs, and program data.

A user can enter commands and information to the computing device 200 through the input device 203. The input device 203 may be, e.g., a keyboard, a touchscreen input device, a touch pad, a mouse, a microphone, and/or a pen.

The computing device 200 may provide its output via the output device 204 which may be, e.g., a monitor or other type of display device, a speaker, or a printer.

The computing device 200, through the network interface 205, may operate in a networked or distributed environment using logical connections to one or more other computing devices, which may be a personal computer, a server, a router, a network PC, a peer device, a smart phone, or any other media consumption or transmission device, and may include any or all of the elements described above. The logical connections may include a network (e.g., the network 150) and/or buses. The network interface 205 may be configured to allow the computing device 200 to transmit and receive data in a network, for example, the network 150. The network interface 205 may include one or more network interface cards (NICs).

Figure 3:
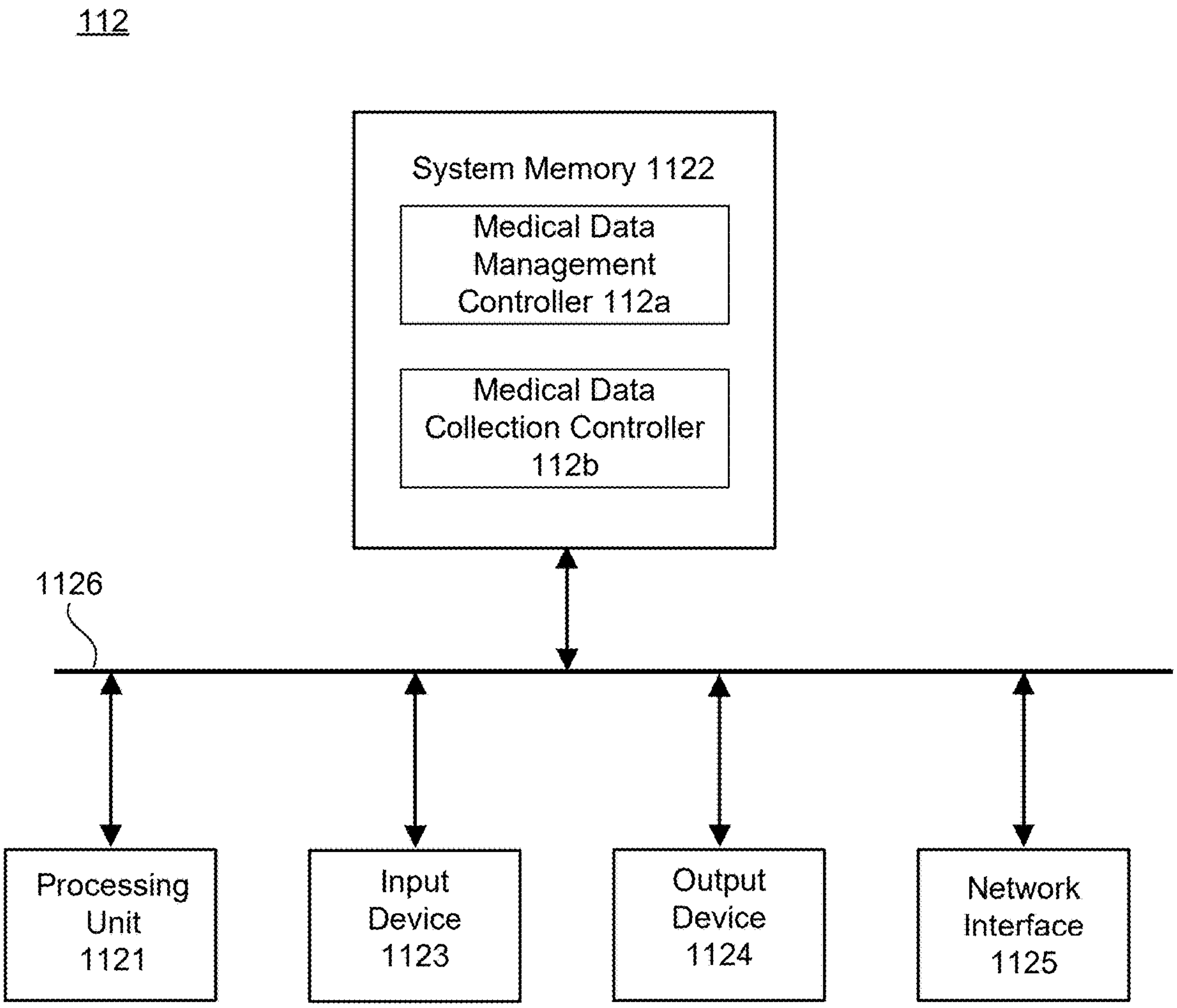
FIG. 3 illustrates an example high level block diagram of the medical data management server according to one embodiment of the present invention.

FIG. 3 illustrates an example high level block diagram of the medical data management server 112 according to one embodiment of the present invention. The medical data management server 112 may be implemented by the computing device 200, and may have a processing unit 1121, a system memory 1122, an input device 1123, an output device 1124, and a network interface 1125, coupled to each other via a system bus 1126. The system memory 1122 may store a medical data management controller 112*a* and a medical data collection controller 112*b*.

In one implementation, the medical data management controller 112*a* may be a Java application. A sponsor user may design a clinical study via the medical data management controller 112*a* and store the study design as definition objects in a repository (e.g., 111*a*). A study design may have multiple elements, including a casebook, groups, events (e.g., patient visits), and forms which include sections, item groups, items, and fields to be filled out.

In one example, a clinical trial is designed to evaluate patient response to a blood pressure medication. Participants on the medication may visit a clinical trial site three times a week for consecutive six weeks. A workflow may be designed for each visit, and may include forms to be filled out, and measurements to be taken. In one example, a participant's blood pressure may be measured three times during each visit, stored in the medical data storage system (e.g., the repository 111*b*) as clinical trial source data, and synchronized with other repositories in the medical data storage system 111 (e.g., the repository 111*a* for the sponsor). In one implementation, only aggregated and obfuscated data, without patient defining information, are sent to the sponsor repository 111*a* and stored there as the EDC data.

A study design may have its own lifecycle. Once a sponsor completes a study design, a workflow may be executed to publish the study design to the participating clinical trial sites (e.g., by storing the study design in clinical trial site repositories 111*b* and 111*c*) and the clinical trial may enter its execution stage. If the study design is amended during the execution stage, the updates may be sent to the participating clinical trial sites (e.g., by synchronizing the updates down to the clinical trial site repositories 111*b* and 111*c*) for them to follow.

Figure 4:
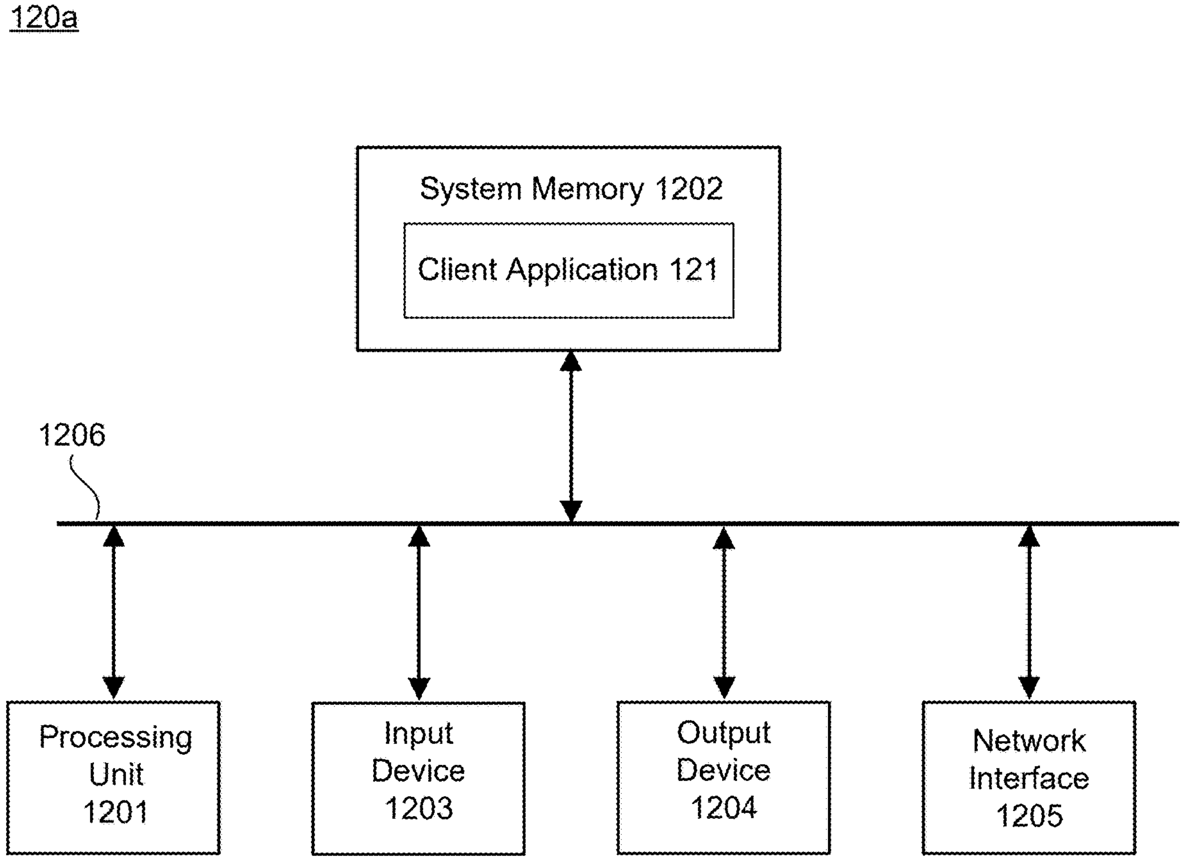
FIG. 4 illustrates an example high level block diagram of a user computing device.

FIG. 4 illustrates an example high level block diagram of a user computing device (e.g., 120*a*) wherein the present invention may be implemented. The user computing device 120*a* may be implemented by the computing device 200 described above, and may have a processing unit 1201, a system memory 1202, an input device 1203, an output device 1204, and a network interface 1205, coupled to each other via a system bus 1206. The system memory 1202 may store the client application 121.

The client application 121 may be an application installed on a computing device, or a web application. Users at a clinical trial site (e.g. local lab) may enter patient clinical trial information via the client application 121, and the clinical trial source data may be stored in a repository (e.g., 111*b*).

Figure 5:
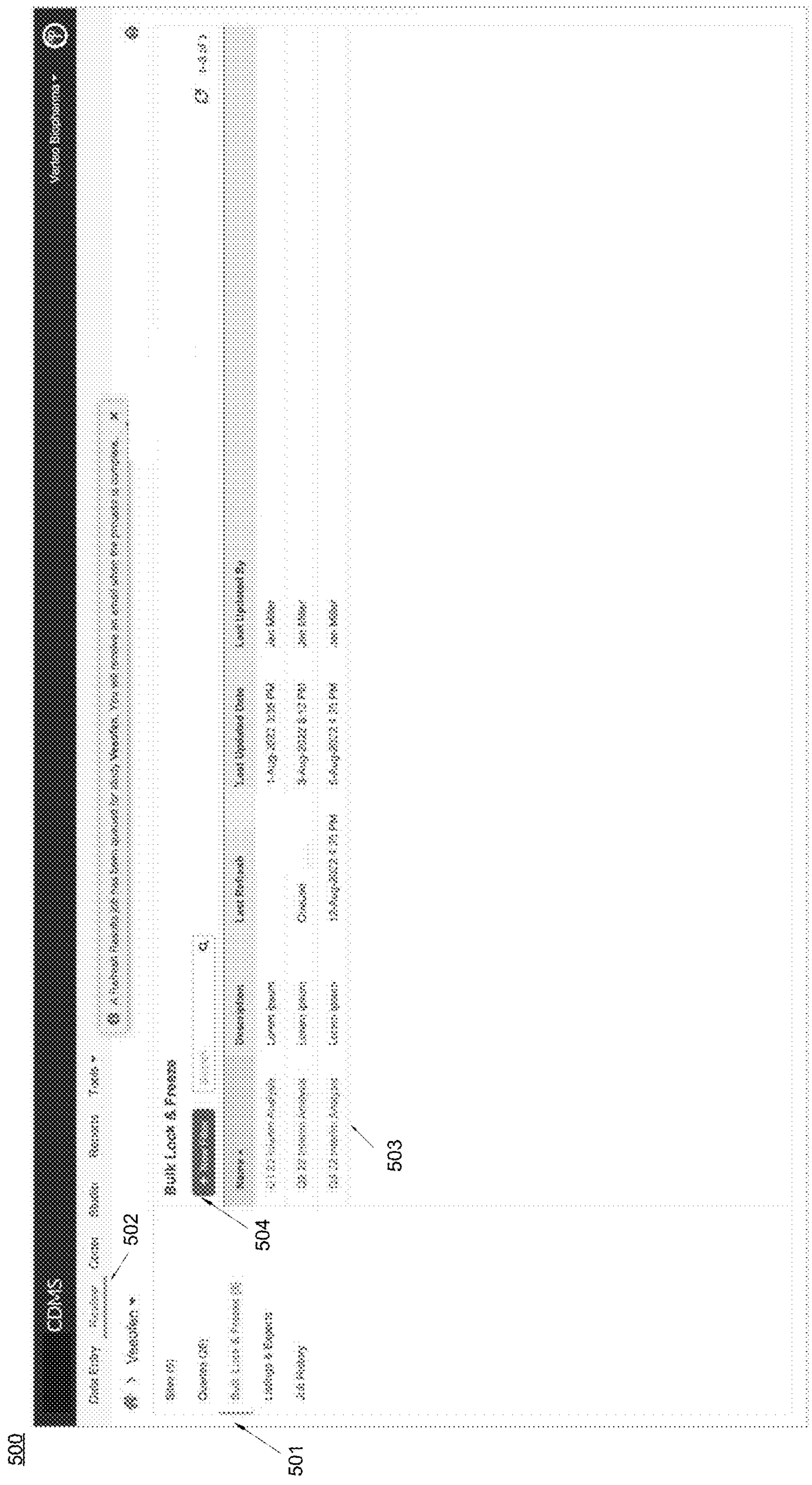
FIG. 5 illustrates an exemplary user interface for managing aggregate data snapshot extractions according to one embodiment of the present invention.

FIG. 5 illustrates an exemplary user interface 500 for generating and managing aggregate data snapshot extractions according to one embodiment of the present invention. When a user (e.g., clinical research associate, data manager, etc.) logs into the medical data management system 110, the aggregate data snapshot tab 501 may be accessed under the data cleaning header 502 which populates a list of previously configured aggregate data snapshot extractions 503 previously stored in the medical data storage system 111. As shown, there is a listing of each aggregate data snapshot extraction with the associated name, description, last refresh date, last updated date, and the user that last performed the update. A new aggregate data snapshot extraction may be configured by accessing the button 504, the details of which will be discussed further below with respect to FIG. 7.

Figure 6:
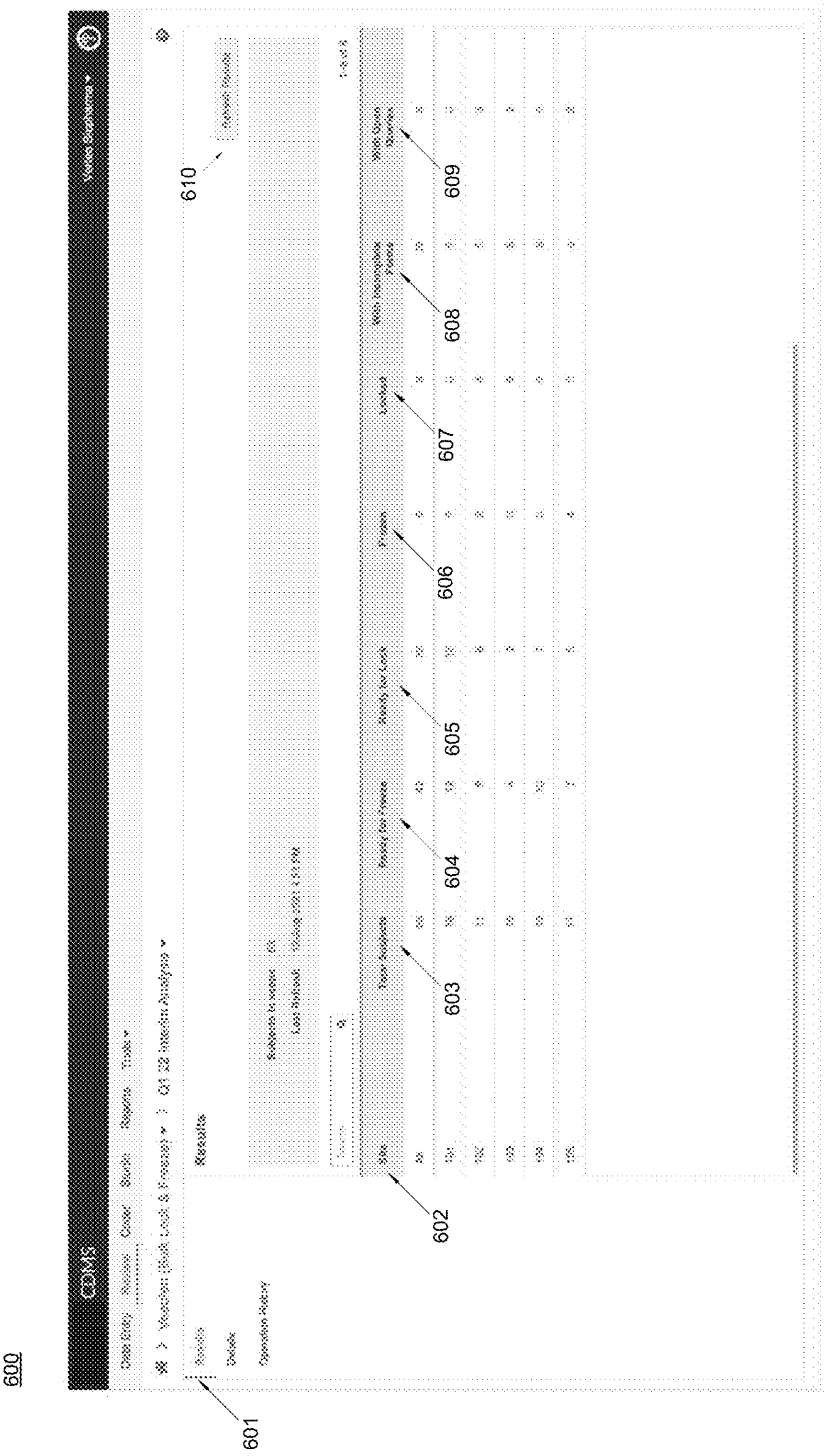
FIG. 6 illustrates an exemplary user interface for cleaning an aggregate data snapshot extraction according to one embodiment of the present invention.

FIG. 6 illustrates an exemplary user interface for cleaning an aggregate data snapshot extraction according to one embodiment of the present invention. Selecting an individual aggregate data snapshot extraction from the list 503 accesses the user interface 600. The medical data management server 112 displays subsets of results that meet certain definitions. Only sites that the user (e.g., clinical research associate or data manager) has access are included in the populated results 601. The sites, or locations/parties that administers contact, screening, and enrollment of eligible patients for clinical research trials, are listed in column 602. The total number of subjects at the site that meet the user configured criteria is displayed in 603. The total number of subjects at the site 603 may be the sum of the additional columns 604-609. The number may be in the form of a link that accesses the populated list of subjects flagged for additional analysis. The subset 604 displays the number of subjects at the site that meet the user configured criteria that is ready to be frozen for additional cleansing. In one implementation, when a clinical trial data entry is frozen, the clinical trial data entry cannot be edited by users at the site. However, the user (e.g., clinical search associate or data manager) can still raise queries on the data and can still perform source data verification ("SDV") which is the process of comparing source data with entered data in the electronic case report form to identify discrepancies to ascertain the source data quality, and data management review ("DMR") which is the process of analysis and verification identify logical discrepancies to make sure the data makes sense. The number of subjects at the site that meet the user configured criteria that is ready to be locked for additional cleansing is displayed in 605. In one implementation, when a clinical trial data entry is locked, the clinical trial data entry cannot be edited at the site, the user (e.g., CRA or DM) cannot raise queries, perform SDV, or DMR. The subset 606 displays the number of subjects at the site that meet the user configured criteria that have already been frozen for additional cleansing. The subset 607 displays the number of subjects at the site that meet the user configured criteria that have already been locked for additional cleansing. The subset 608 displays the number of subjects at the site that meet the user configured criteria, but have one or more incomplete items on the submitted forms. The subset 609 displays the number of subjects at the site that meet the user configured criteria, but have one or more open queries that have yet to be resolved. Additional columns that are not displayed that may be included are: a total number of subjects at the site that meet the user configured criteria that have forms or event dates that require an additional signature or verification, a total number of subjects at the site that meet the user configured criteria that have forms or event dates that require SDV, a total number of subjects at the site that meet the user configured criteria that have forms or event dates that require DMR. Additional entries may have been added, or fields modified that meet the user configured criteria since the last refresh date of the aggregate data snapshot extraction. Button 610 may be used to update the numbers to accurately reflect the current state.

Figure 7:
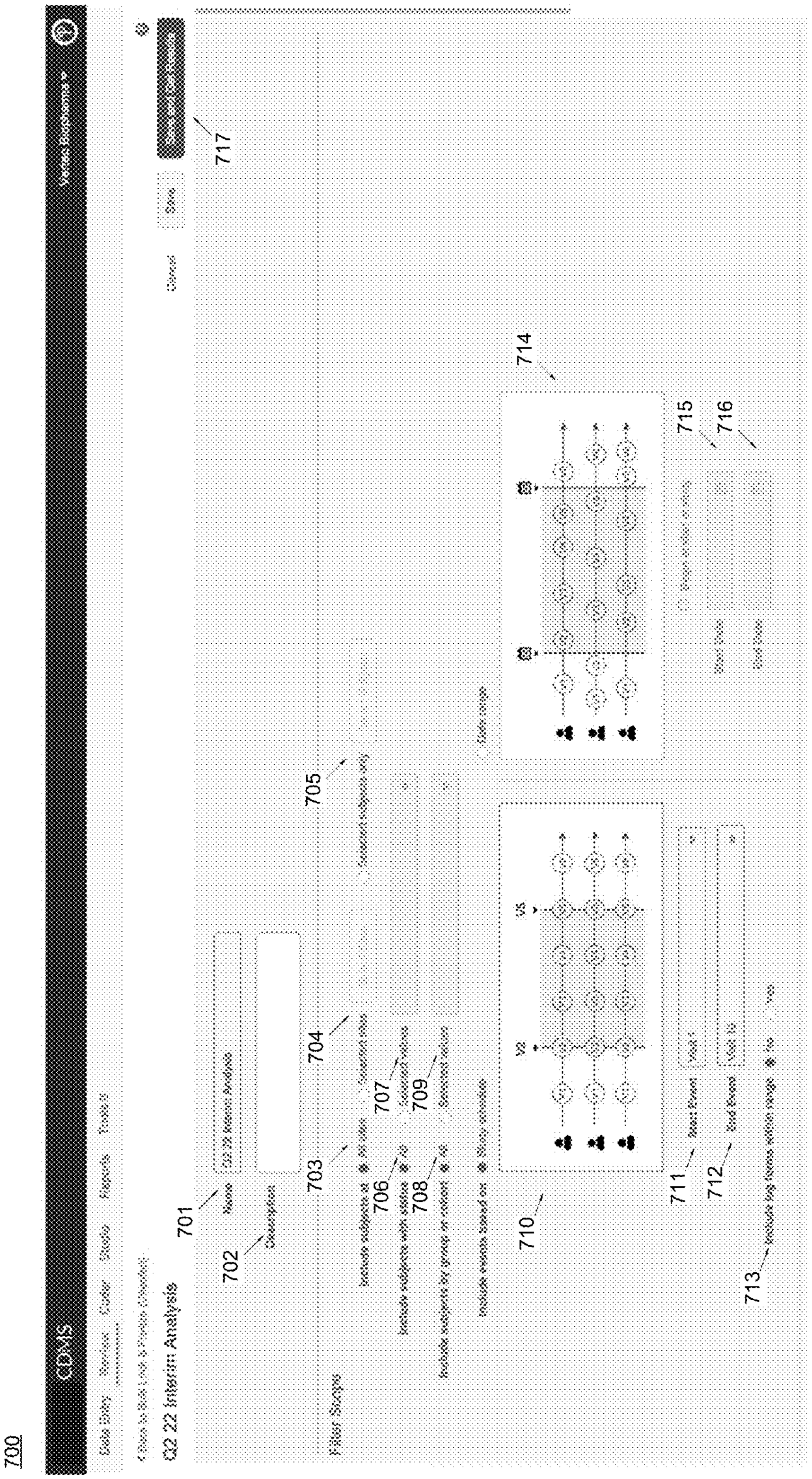
FIG. 7 illustrates an exemplary user interface for configuring an aggregate data snapshot extraction according to one embodiment of the present invention.

FIG. 7 illustrates an exemplary user interface 700 for configuring an aggregate data snapshot extraction according to one embodiment of the present invention. There may be a field to enter a name 701 and description 702 for the aggregated data snapshot extraction. The user (e.g., clinical research associate, data manager, etc.) may configure the aggregated data snapshot extraction to include subjects at all sites 703, only selected sites 704, or only selected subjects 705. The subjects can be further limited to include all subjects regardless of status 706, or subjects with certain selected statuses 707. Exemplary statuses may include screen failure, discontinued, enrolled, randomized, consented, etc. The subjects may also be limited to include all subjects regardless of treatment arm, group or cohort 708, or subjects belonging with certain selected treatment arms, groups or cohorts 709.

In one implementation, the user (e.g., clinical research associate, data manager, etc.) may configure the aggregated data snapshot extraction to include events based on study schedule 710. Events can be extracted if they fall between a certain specified start event 711 and a certain specified end event 712. Start and end sequence number can be entered for repeating events. An example would be to extract entries between the subject's treatment cycle (2) and the subject's third visit. Events can be further limited by including log forms (e.g., dosing, EKG, hematology, Adverse Events, Medical History, etc.) within the above specified range 713.

In one implementation, a user may want to freeze or lock a specified number of visits for all subjects. For instance, there may be an interim database lock scheduled, where data sets obtained in a clinical trial are finalized. After data collection has been completed, there may be follow up of all participants, data quality and validation exercises undertaken. The data will need to be cleaned, SDV performed, and then locked. However, data entry in visits after the interim database lock scheduled may still occur.

In another implementation, the user (e.g., clinical research associate, data manager, etc.) may configure the aggregated data snapshot extraction to include events based on a date range 714. Events can be extracted if they fall between the start of the study, a certain specified start date 715, or a certain specified end date 716. Any of the above configurations may be used individually, or in combination to extract relevant aggregated data for cleaning.

Figure 8:
FIG. 8 illustrates an exemplary user interface for configuring an aggregate data snapshot extraction according to another embodiment of the present invention.

In one implementation, a user (e.g., clinical research associate, data manager, etc.) with a computing device (e.g. 120*a*) may utilize the graphical user interface 800 depicted in FIG. 8 to verify and edit the configuration settings for an aggregate data snapshot extraction according to one embodiment of the present invention. The graphical user interface 800 may be accessed by navigating the tab 801. Button 802 may be used to update the configuration settings for an aggregate data snapshot extraction. Ready states are displayed at 803, which in addition to the above settings, describe the criteria for freezing or locking a data entry. Criteria options may include: all events and forms complete, all queries answered, all queries closed, all event dates and forms SDV complete, all event dates and forms DMR complete, all event dates and forms signed.

Figure 9:
FIG. 9 illustrates an exemplary user interface for configuring the optimized bulk lock, edit, and freeze for an aggregate data snapshot extraction according to one embodiment of the present invention.

In one implementation, a user (e.g., clinical research associate, data manager, etc.) with a computing device (e.g. 120*a*) may utilize the graphical user interface 900 depicted in FIG. 9 to track optimized bulk lock, edit, and freeze actions for various aggregate data snapshot extractions according to one embodiment of the present invention. There may be a list of aggregate data snapshot extractions 901 with associated operation type, status, user, site, subjects affected, and creation date. The icon 902 may be utilized to open the associated aggregate data snapshot extraction to continue the data cleansing process. The icon 903 may be utilized to download an aggregate data snapshot extraction that has completed the cleansing process.

Figure 10:
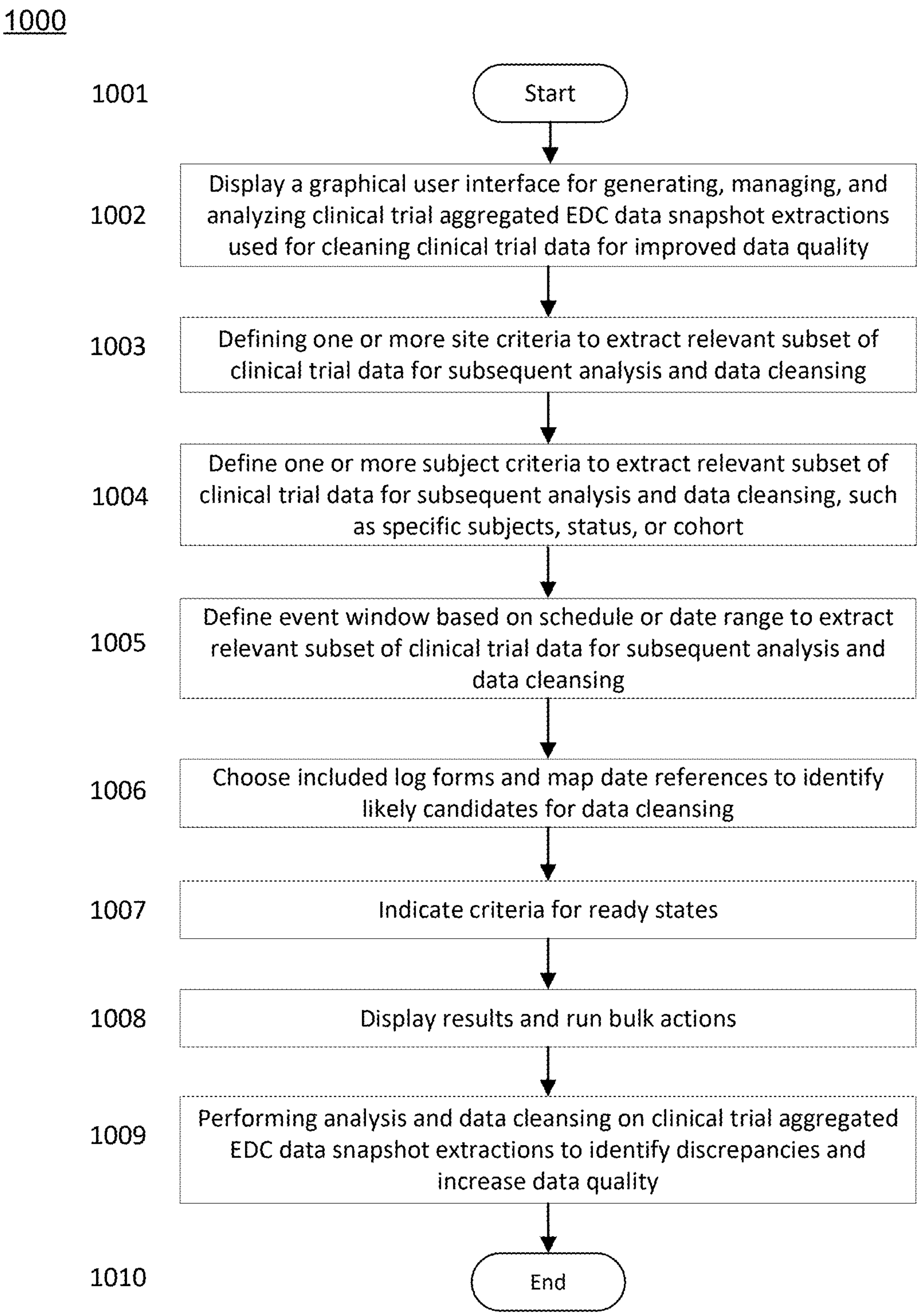
FIG. 10 illustrates an example flowchart of a method for aggregate data snapshot extraction and optimized bulk lock, edit and freeze according to one embodiment of the present invention.

FIG. 10 illustrates an example flowchart of a method for aggregate data snapshot extraction and optimized bulk lock, edit and freeze according to one embodiment of the present invention. The process beings at 1001. In certain disclosed embodiments, the system calls upon a server that, in operation, serves interface pages to users for aggregating medical-related data, e.g. EDC data from labs pertaining to clinical trials. A database is maintained (e.g., the medical data storage system 111) by an administrative entity, that, in operation stores and aggregates EDC data from labs pertaining to clinical trials.

At 1002, a graphical user interface for extracting an aggregate data snapshot for optimized bulk lock, edit and freeze is displayed. In one embodiment, as described above in FIG. 5 aggregated data snapshot extractions can be managed and maintained.

At 1003, the user (e.g., clinical research associate, data manager, etc.) with a computing device (e.g., 120*a*) may utilize the graphical user interface depicted in FIG. 7 to define one or more site criteria to extract relevant subset of clinical trial data for subsequent analysis and data cleansing. The medical data management server 112 may extract entries configured by the user from the medical data storage system 111 satisfying the criteria of all sites the user has access. In another embodiment, specific sites may be selected and the medical data management server 112 may extract entries from the medical data storage system 111 for the sites specified.

At 1004, the user (e.g., clinical research associate, data manager, etc.) with a computing device (e.g., 120*a*) may utilize the graphical user interface depicted in FIG. 7 to define one or more subject criteria to extract relevant subset of clinical trial data for subsequent analysis and data cleansing. In one implementation, the user may define the aggregated data snapshot extraction to include subjects with certain status, subjects by treatment arms, group or cohort, etc. The medical data management server 112 may extract entries configured by the user from the medical data storage system 111 satisfying the subject criteria for the sites the user has access previously defined in 1003.

At 1005, the user (e.g., clinical research associate, data manager, etc.) with a computing device (e.g., 120*a*) may utilize the graphical user interface depicted in FIG. 7 to define an event window based on a study schedule or date range to extract relevant subset of clinical trial data for subsequent analysis and data cleansing. In one implementation, the user may define the aggregated data snapshot extraction to include only events from a specified start event on the clinical study schedule to a specified end event on the clinical study schedule. The medical data management server 112 may extract entries configured by the user from the medical data storage system 111 satisfying the event criteria for the sites the user has access as previously defined in 1003 and subjects the user previously defined in 1004.

In another implementation, the user may define the aggregated data snapshot extraction to include only events from a specified start calendar date to a specified end calendar date. The medical data management server 112 may extract entries configured by the user from the medical data storage system 111 satisfying the event criteria for the sites the user has access previously defined in 1003 and subjects the user previously defined in 1004.

At 1006, the user (e.g., clinical research associate, data manager, etc.) with a computing device (e.g., 120*a*) may utilize the graphical user interface depicted in FIG. 7 to include and define log forms and map data references to identify relevant subset of clinical trial data for subsequent analysis and data cleansing. The medical data management server 112 may extract entries configured by the user from the medical data storage system 111 satisfying the criteria for the sites the user has access previously defined in 1003, subjects the user previously defined in 1004, and events the user previously defined in 1005.

At 1007, the user (e.g., clinical research associate, data manager, etc.) with a computing device (e.g., 120*a*) may utilize the graphical user interface depicted in FIG. 7 to indicate criteria for ready states. Ready states, which in addition to the above settings, describe the criteria for freezing or locking a data entry. Criteria options may include: all events and forms complete, all queries answered, all queries closed, all event dates and forms SDV complete, all event dates and forms DMR complete, all event dates and forms signed.

At 1008, the medical data management server 112 extracts entries configured by the user from the medical data storage system 111 satisfying the criteria defined above and displays the results as an aggregated data snapshot extraction as depicted in FIG. 6.

At 1009, the user (e.g., clinical research associate, data manager, etc.) with a computing device (e.g., 120*a*) may utilize the graphical user interface depicted in FIG. 6 to analyze, edit and clean the bulk locked/frozen data from 1008. The method ends at 1010.

The above-described features and applications can be implemented as software processes that are specified as a set of instructions recorded on a computer readable storage medium (also referred to as computer readable medium). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

These functions described above can be implemented in digital electronic circuitry, in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

In this specification, the term "software" is meant to include firmware residing in read-only memory or applications stored in magnetic storage, which can be read into memory for processing by a processor. Also, in some implementations, multiple software technologies can be implemented as sub-parts of a larger program while remaining distinct software technologies. In some implementations, multiple software technologies can also be implemented as separate programs. Finally, any combination of separate programs that together implement a software technology described here is within the scope of the subject technology. In some implementations, the software programs, when installed to operate on one or more electronic systems, define one or more specific machine implementations that execute and perform the operations of the software programs. Examples of computer programs or computer code include machine code, for example is produced by a compiler, and files including higher-level code that are executed by a computer, an electronic component, or a microprocessor using an interpreter.

A computer program (also known as a program, software, software application, script, or code) can be written in any form of programming language, including compiled or interpreted languages, declarative or procedural languages, and it can be deployed in any form, including as a stand alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

As used in this specification and any claims of this application, the terms "computer", "server", "processor", and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

It is understood that any specific order or hierarchy of steps in the processes disclosed is an illustration of example approaches. Based upon design preferences, it is understood that the specific order or hierarchy of steps in the processes may be rearranged, or that all illustrated steps be performed. Some of the steps may be performed simultaneously. For example, in certain circumstances, multitasking and parallel processing may be advantageous. Moreover, the separation of various system components illustrated above should not be understood as requiring such separation, and it should be understood that the described program components and systems can generally be integrated together in a single software product or packaged into multiple software products.

Various modifications to these aspects will be readily apparent, and the generic principles defined herein may be applied to other aspects. Thus, the claims are not intended to be limited to the aspects shown herein, but is to be accorded the full scope consistent with the language claims, where reference to an element in the singular is not intended to mean "one and only one" unless specifically so stated, but rather "one or more." Unless specifically stated otherwise, the term "some" refers to one or more.

The invention claimed is:

1. A computer-implemented method for optimized processing of clinical trial data in a clinical trial management system, the method enabling bulk data management operations across multiple casebooks, the method comprising:

enabling display of a user interface for managing aggregated clinical trial source data, wherein the clinical trial source data is clinical trial data obfuscated to remove patient defining information and stored as electronic data capture (EDC) data in a first repository in the clinical trial management system, wherein the clinical trial source data is received from a plurality of clinical trial site repositories, each clinical trial site repository storing clinical trial source data from a respective clinical trial site, and the clinical trial source data is converted to the EDC data by a medical data management server before being stored in the first repository, wherein data in the plurality of clinical trial site repositories is synchronized with the first repository when new data entries are received from user computing devices;

defining one or more site criteria, wherein the site criteria includes a selected subset of sites that are flagged with clinical trial source data of interest for subsequent analysis and data cleansing;

defining one or more subject criteria, wherein the subject criteria includes a selected subset of subjects that are flagged with clinical trial source data of interest for subsequent analysis and data cleansing;

defining an event window, wherein the event window includes a selected subset of clinical trial study schedule events of interest for subsequent analysis and data cleansing;

identifying log forms for specified date references that are flagged with clinical trial source data of interest for subsequent analysis and data cleansing;

identifying one or more criteria for ready states, wherein the ready states include conditions that require additional user action before restricting data management operations;

extracting, by the medical data management server, from the first repository in the clinical trial management system clinical trial source data that fulfills the defined site criteria, the defined subject criteria, the defined event window, the identified log forms for specified date references, and the identified criteria for ready states to form an aggregated clinical trial data snapshot;

displaying the aggregated clinical trial data snapshot on the user interface, wherein the clinical trial data snapshot includes a table of clinical trial source data entries organized by site, the table displaying for each site a total number of subjects at the site that meet the defined criteria and numerical subsets comprising a number of subjects ready to be frozen, a number of subjects ready to be locked, a number of subjects already frozen, and a number of subjects already locked;

restricting data management operations in bulk across a plurality of casebooks, thereby replacing piecemeal subject-by-subject data locking with efficient bulk operations, for each of the extracted clinical trial source data entries in the aggregated clinical trial data snapshot that fulfills the defined site criteria, the defined subject criteria, the defined event window, the identified log forms for specified date references, and the identified criteria for ready states;

displaying a listing of the restricted data management operations for the extracted clinical trial source data along with a corresponding progress status for each operation on a second user interface, wherein the restricting of data management operations include: 1) freezing the extracted clinical trial source data entries such that users can still open queries, and perform source data verification and data management review, 2) unfreezing the extracted clinical trial source data entries, 3) locking the extracted clinical trial source data entries such that users cannot open queries, perform source data verification and data management review, and 4) unlocking the extracted clinical trial source data entries; and cleaning each of the extracted clinical trial source data entries in the aggregated clinical trial data snapshot.

2. The computer-implemented method of claim 1, wherein the one or more subject criteria relates to at least one of: status, group, cohort, or treatment arm.

3. The computer-implemented method of claim 1, wherein the selected subset of subjects are flagged based on screen failure and withdrawn statuses.

4. The computer-implemented method of claim 1, wherein the selected subset of clinical trial study schedule events are determined from a calendar date range to identify clinical trial source data of interest.

5. The computer-implemented method of claim 1, wherein the selected subset of clinical trial study schedule events is selected using one or more of the following: prescreen visit, screening visit, baseline visit, treatment cycle day 1, treatment cycle day 7, treatment cycle day 14, treatment cycle day 21, treatment cycle day 28, end of treatment visit, and final visit.

6. The computer-implemented method of claim 1, wherein the log forms include documents recording adverse events, concomitant medications, and medical history.

7. The computer-implemented method of claim 1 wherein the specified date ranges for the log forms include start and end dates selected from the following: creation date, last updated date, submission date, entry information start date, entry information end date, and treatment date.

8. The computer-implemented method of claim 1, wherein the log forms include forms tracking dosing, EKG, hematology, informed consent, medical history, physical exam, subject info, and vitals.

9. The computer-implemented method of claim 1, wherein the ready states include identifying any incomplete forms.

10. The computer-implemented method of claim 1, wherein the ready states include identifying any open queries.

11. The computer-implemented method of claim 1, wherein the ready states include identifying any entries that require source data verification (SDV).

12. The computer-implemented method of claim 1, wherein the ready states include identifying any entries that require data management review (DMR) to locate logical discrepancies within the clinical trial source data.

13. The computer-implemented method of claim 1, wherein the ready states include identifying any entries that require additional signatures or verification.

14. The computer-implemented method of claim 1, further comprising: updating the clinical trial source data in the aggregated clinical trial data snapshot and storing the updated clinical trial source data in a second repository in the clinical trial management system.

15. The computer-implemented method of claim 1, further comprising: rescinding the restriction of data management operations for the extracted clinical trial source data that fulfills the defined site criteria, the defined subject criteria, the defined event window, the identified log forms for specified date references, and the identified criteria for ready states.

16. The computer-implemented method of claim 1, wherein the user interface is on a first user computing device in the clinical trial management system.

* * * * *